US006747058B1

(12) United States Patent
Dedhiya et al.

(10) Patent No.: US 6,747,058 B1
(45) Date of Patent: Jun. 8, 2004

(54) STABLE COMPOSITION FOR INHALATION THERAPY COMPRISING DELTA-9-TETRAHYDROCANNABINOL AND SEMIAQUEOUS SOLVENT THEREFOR

(75) Inventors: Mahendra G. Dedhiya, Dublin, OH (US); Julia J. Economou, HIlliard, OH (US); Andrea M. McPhillips, Columbus, OH (US); Beverley A. Wynne, Worthington, OH (US)

(73) Assignee: Unimed Pharmaceuticals, Inc.

( * ) Notice: Subject to any disclaimer, the term of this patent is extended or adjusted under 35 U.S.C. 154(b) by 107 days.

(21) Appl. No.: 09/639,289

(22) Filed: Aug. 15, 2000

Related U.S. Application Data

(60) Provisional application No. 60/150,023, filed on Aug. 20, 1999.

(51) Int. Cl.$^{7}$ ........................ A01N 43/16; A01N 25/02; A61K 31/35; A61K 4/00; A61L 9/04

(52) U.S. Cl. .......................................... 514/454; 424/43

(58) Field of Search ............................ 424/43; 514/454

(56) References Cited

U.S. PATENT DOCUMENTS

| | | | | |
|---|---|---|---|---|
| 4,635,651 A | | 1/1987 | Jacobs | |
| 4,933,363 A | | 6/1990 | ElSohly | |
| 5,258,336 A | * | 11/1993 | LaMastro et al. | 501/66 |
| 5,447,729 A | | 9/1995 | Belenduik et al. | |
| 5,492,688 A | | 2/1996 | Byron et al. | |
| 5,502,076 A | | 3/1996 | Dixit et al. | |
| 5,508,023 A | | 4/1996 | Byron et al. | |
| 5,508,037 A | | 4/1996 | ElSohly | |
| 5,540,934 A | * | 7/1996 | Touitou | 424/450 |
| 5,635,530 A | | 6/1997 | Mechoulam et al. | |
| 5,716,638 A | * | 2/1998 | Touitou | 424/450 |
| 5,736,124 A | | 4/1998 | Akehurst et al. | |
| 5,804,592 A | | 9/1998 | Volicer | |
| 5,847,128 A | | 12/1998 | Martin et al. | |
| 5,874,443 A | * | 2/1999 | Kiely et al. | 514/309 |
| 5,916,540 A | | 6/1999 | Akehurst et al. | |
| 5,922,306 A | | 7/1999 | Akehurst et al. | |
| 5,939,429 A | | 8/1999 | Kunos et al. | |
| 6,162,829 A | * | 12/2000 | Burstein | 514/570 |
| 6,294,192 B1 | * | 9/2001 | Patel et al. | 424/451 |

FOREIGN PATENT DOCUMENTS

| | | |
|---|---|---|
| WO | WO 98/29096 A1 | 7/1998 |
| WO | WO 99/32107 A1 | 7/1999 |
| WO | WO 00/24362 A2 | 5/2000 |
| WO | WO 00/27359 A1 | 5/2000 |
| WO | WO 01/13886 A1 | 3/2001 |

OTHER PUBLICATIONS

Allison's Apothecary. Our Amber Glass Bottles. 1999.*

Williams, et al., "Bronchodilator Effect of Delta–Tetrahydrocannabinol Administered By Aerosol to Asthmatic Patients," Thorax, vol. 31 (No. 6), p. 720–723, (1976).

Lichtman, et al., "Pharmacological Evaluation of Aerosolized Cannabinoids in Mice," European Journal of Pharmacology, vol. 399 (No. 2–3), p. 141–149, (2000).

Ault, "Techniques and Experiments for Organic Chemistry," Waveland Press, Inc. (Prospect Heights, Illinois), p. 44–50, 183–194, (1987).

"Aerosol Delivery: Stability Data" (Feb. 18, 1998).

Dedhiya, et al., "Current Concepts for Delivery of D–9 THC: Prospects For Cannabinoid Drug Development," (1998).

Vachon, et al., "Airways Response to Aerosolized Delta–9–Tetrahydrocannabinol: Preliminary Report," The Therapeutic Potential of Marihuana, Plenum Medical Book Company (New York and London), p. 111–121, (1976).

Fratello, "NIH Study Helps the Case For Medical Marijuana," The Sacremento Bee, (Sep. 5, 1997).

Lewis, "Just Say 'Research'," The Scientist, vol. 12 (No. 3), p. 1&6, (Feb. 2, 1998).

Little, "Studies of Stability and Purification of Delta 9–Tetrahydrocannabinol," (Nov. 1970).

Garrett, et al., "Physicochemical Properties, Solubility, and protein Binding of Delta 9–Tetrahydrocannabinol," Journal of Pharmaceuticall Sciences, p. 1056–1064, (1974).

Ohlsson, et al., "Plasma Delta–9–Tetrahydrocannabinol Concentrations and Clinical Effects After Oral and Intravenous Administration and Smoking," Clinical Pharmacology and Therapeutics, vol. 28 (No. 3), p. 409–416, (Sep. 1980).

Perez–Reyes, et al., "Pharmacology of Orally Administered Delta–9–Tetrahydrocannabinol," Clinical Pharmacology and Therapeutics, vol. 14 (No. 1), p. 48–55, (1973).

Tashkin, et al., "Bronchial Effects of Aerosolized Dleta–9–Tetrahydrocannabinol in Healthy and Asthmatic Subjects," American Review of Respiratory Disease, p. 57–65, (1977).

Vachon, L. et al, Airways Response to Aerosolized Delta–9–Tetrahydro–Cannabinol: Prliminary Report, The Therepeutic Potential of Marihuana, 1976, Chapter 8, 111–121, Plenum Medical Book Company, New York, US.

Williams, S.J. et al, Bronchodilator effect of delta–tetrahydrocannabinol administered by aerosol to asthmatic patients, Thorax, 1976, 720–723, vol. 31, No. 6.

Lichtman, A. et al, Pharmacological evaluation of aerosolized cannabinoids in mice, Europeon Journal of Phamacology, 2000, 141–149, vol. 399, No. 2–3.

* cited by examiner

*Primary Examiner*—Sreeni Padmanabhan
*Assistant Examiner*—Lauren Q. Wells
(74) *Attorney, Agent, or Firm*—Mayer, Brown, Rowe & Maw LLP; Joseph A. Mahoney

(57) ABSTRACT

A formulation of delta-9-tetrahydrocannabinol in a semi-aqueous solvent, such as 35:10:55 alcohol:water:propylene glycol (v/v), produces a stable clear solution near the solubility point of the drug. Because delta-9-tetrahydrocannabinol has poor affinity for the formulation, it is able to partition out and transport across cell membranes to reach the bloodstream quickly. This has been demonstrated by the comparative $t_{max}$ values achieved in single dose intravenous and 14 day multiple dose inhalation studies conducted in dogs and rats.

20 Claims, No Drawings

STABLE COMPOSITION FOR INHALATION THERAPY COMPRISING DELTA-9-TETRAHYDROCANNABINOL AND SEMIAQUEOUS SOLVENT THEREFOR

This application claims the benefit of Provisional application Ser. No. 60/150,023, filed Aug. 20, 1999.

BACKGROUND OF THE INVENTION

1. Field of the Invention

The present invention relates to a fast-acting delivery system for delta-9-tetrahydrocannabinol (dronabinol) to improve bioavailability. More particularly, it provides a stable composition for delivery by inhalation to the lungs, and subsequently to the bloodstream, the composition comprising an a therapeutically effective amount of delta-9-tetrahydrocannabinol (also known as "delta-9-THC") and a pharmaceutically-acceptable semiaqueous solvent.

2. Statement of the Related Art

Delta-9-tetrahydrocannabinol is currently approved by regulatory authorities for use as an antiemetic in cancer chemotherapy as well as an appetite stimulant for patients inflicted with the AIDS virus. The product is currently marketed under the name MARINOL® (dronabinol) as an oral soft gelatin capsule in which the drug substance is dissolved in sesame oil.

Bioavailability of the current formulation ranges from 10–20% due to a high first pass metabolism associated with oral administration. The current formulation has an onset of action ranging from 0.5 to 1 hour. It would be desirable to improve bioavailabity and quicken onset of action for the above indications as well as for the treatment of alternative conditions, such as spinal cord spasticity, glaucoma; and Alzheimer's disease. Alternative routes previously suggested to overcome oral delivery limitations include the administration of drugs (including delta-9-tetrahydrocannabinol) through the inhalation route. It has been demonstrated in the literature, for example, that smoking marijuana cigarettes (the main constituent being dronanbinol, i.e., delta-9-THC) has shown improved bioavailability (60–70%). However, there are obvious disadvantages relating to smoking marijuana, including raw material impurities, depression of alveolar macrophage activity, and bronchial irritation. Another approach suggested in initial reports at a meeting on Feb. 24, 1998, sponsored by the Institute of Medicine, National Academy of Sciences, Division of Neuroscience and Behavioral Health in Washington, D.C., was to study and use particle size data developed in a conventional nebulizer system to try to enhance bioavailability of delta-9-tetrahydrocannabinol after deep lung route of administration. Among the suggested routes of administration suggested by the prior art are those using aerosol formulations to be inhaled as described in Volicer, U.S. Pat. No. 5,804,592, granted Sep. 8, 1998, based on Provisional Application priority May 7, 1997. However, as presently advised, there has been no prior disclosure of experiments which used formulations comprising delta-9-tetrahydrocannabinol and semiaqueous solvents comprising judiciously selected volumetric ratios of alcohol, water and pharmaceutically-acceptable glycols to enhance partitioning, and no evidence of enhanced bioavailability in warm-blooded animals, including humans, has been known for such compositions prior to the present invention. It still remains desirable, therefore, to develop a new safe, fast acting delivery system for delta-9-tetrahydrocannabinol to improve bioavailability, and such a system is the subject matter of the present invention.

SUMMARY OF THE INVENTION

In accordance with the present invention there are provided stable compositions for rapid delivery by inhalation to the lungs, and subsequently to the bloodstream, the compositions comprising a therapeutically effective amount of delta-9-tetrahydrocannabinol in a pharmaceutically-acceptable semiaqueous solvent comprising an alcohol, water and a glycol, in relative volumetric amounts sufficient (i) to aerosolize the composition to a mean mass median aerodynamic diameter in the range of from about 1 up to about 10 μM; and (ii) to enhance partitioning by producing a stable clear solution near the solubility point of the delta-9-tetrahydrocannabinol.

Among the preferred features of the invention are such compositions wherein the delta-9-tetrahydrocannabinol comprises from about 0.1 to about 200 mg/mL, and especially 25 and 50 mg/mL;

the solvent comprises ethanol, water and propylene glycol;

the volumetric ratios of ethanol:water:propylene glycol are selected from those in the range of from 10–70:10–30:20–80, respectively, having a combined total of 100;

the volumetric ratios of ethanol:water:propylene glycol are selected from those in the range of from 10–70:10:20–80, respectively, having a combined total of 100;

the volumetric ratios of ethanol:water:propylene glycol are 35:10:55, respectively, having a combined total of 100.

Also contemplated by the present invention are sterile or preserved sealed unit- and/or multi-unit dosage forms of delta-9-tetrahydrocannabinol comprising a container and a stable composition for rapid delivery by inhalation to the lungs and subsequently to the bloodstream, as first defined above, and especially those wherein the container comprises Type I Amber Glass with a suitable liner.

DETAILED DESCRIPTION OF THE INVENTION

Numerous experiments have shown that the drug formulation is critical for delta-9-tetrahydrocannabinol to be effectively delivered to the lung rapidly. It has been discovered that the formulations of the present invention must be stable, aerosolize to a particle size less than or equal to 10 μM to reach the lung, and the drug must readily partition out of the delivery system in order to transport across biological membranes and reach the blood stream.

The physico-chemical characteristics of delta-9-tetrahydrocannabinol raw drug material lend themselves to various formulations, including solutions. Delta-9-tetrahydrocannabinol is virtually insoluble in water (0.003 g/mL). It is known that the drug substance is extremely lipophilic, with a reported oil/water coefficient of 9,400,000 (Garret and Hunt, Journal of Pharmaceutical Sciences, Vol. 63, No. 7, pages 1056–1064, 1974; and Thomas et al., The Journal of Pharmacology and Experimental Therapeutics, Vol. 255, No. 1, pages 624–630, 1990). These factors have been considered in developing the compositions of this invention.

Also critical to the present invention is the need for selecting substances which will release the drug for absorption or partition it from the dosage form. The lipophilic nature of delta-9-tetrahydrocannabinol suggests that formulations made primarily of lipophilic excipients such as oils, such as sesame seed oil, currently approved for oral unit dosage use, would not be desirable because the drug would not partition readily. In the case of oily excipients, delta-9-tetrahydrocannabinol would have a strong affinity for the formulation and would slowly partition out, resulting in slow absorption, exactly the problem sought to be avoided.

Semiaqueous solutions, that is combinations of organic solvents with small, effective amounts of water, lend themselves to making formulations with delta-9-tetrahydrocannabinol with unexpected increases in partitioning, apparently because the drug has a poor affinity for the water within the formulation. Because of the increased ease of partitioning, once released deeply in the lung from the dosage forms of the present invention, delta-9-tetrahydrocannabinol is able to cross cell membranes rapidly, traverse the alveolar epithelial cells, interstitium, and endothelium to reach the blood stream (Thompson, "Pharmacology of Therapeutic Aerosols" Chapter 2, in Pharmaceutical Inhalation Aerosol Technology, Ed. Hickey, Marcel Dekker, Inc. New York, pages 29–37, 1992). As a further advantage, the formulations of delta-9-THC and semiaqueous solvents of the present invention may be aerosolized more easily than oil based systems.

As will be shown hereinafter, delta-9-tetrahydrocannabinol readily dissolves in ethanol and in equal parts of ethanol and propylene glycol to form clear solutions which, for purposes of the present invention, are "stable" that is, remain clear through three cycles of freeze/thaw. Such compositions, however, do not meet the ease of partitioning required by the present invention because the delta-9-tetrahydrocannabinol prefers to stay in the organic phase and only slowly releases itself from the dosage form at the intended site of absorption. As will also be described in detail hereinafter, water can be added to the organic phase, and the delta-9-tetrahydrocannabinol is able to remain in solution, near the solubility point of the drug, and, unexpectedly, partitioning is enhanced and in vivo bioavailability is accelerated, especially in comparison with i.v. administration of the same formulation. The experiments have also shown that as the water content of the semiaqueous solvent increases and the ethanol content decreases beyond a certain level, the drug readily falls out of solution, and such unstable formulations no longer function as dosage forms within the scope of the invention.

The citation to Thomas, mentioned above, teaches that aerosol particle size has an influence on the deposition pattern of many drugs in the lung. In general, deposition is successful at a mean mass median aerodynamic diameter in the range of from about 1 $\mu$M to about 10 $\mu$M. For best results in lung delivery, it is known from Thomas that delta-9-tetrahydrocannabinol should be targeted for delivery deep in the lung, and this is facilitated by using aerosol particle diameters of less than about 3 $\mu$M, a size which is readily, but unexpectedly, obtained with the compositions of the present invention, using conventional nebulizers, as will be shown in the examples which follow, and in conventional metered dose inhalers.

To make the formulations of the present invention, it is preferred, but not essential, to dissolve, per mL of final composition, 1–250 mg of delta-9-tetrahydrocannabinol (dronabinol), USP in 5–95% v/v of ethanol, USP (190 proof), or an obvious equivalent, e.g., isopropanol, in a suitable mixer; to add 20–80% v/v propylene glycol, USP, or an obvious equivalent, such as polypropylene glycol, polyethylene glycol, and the like, and 10–25% v/v purified water and mix, and then filter and transfer to a storage tank. A suitable concentration of delta-9-tetrahydrocannabinol in pharmaceutical compositions for inhalation is 0.05 to 15% (by weight). A preferred concentration is from 0.02 to 5%. A more preferred concentration is from 0.1 to 4%. The formulations of the invention can also include minor but effective amounts of anti-oxidants, surfactants, buffers, sodium chloride, pH adjusting agents, bacteriostats, stabilizers, preservatives, and the like.

To package the formulations of the present invention, the formulations are transferred by conventional means to unit-dose or multi-dose sealed containers, such as ampules and vials, preferably made of amber glass Types I, II and III, more preferably Type I, with a suitable liner.

To use the formulations of the present invention, the quantity of delta-9-tetrahydrocannabinol can vary widely. For example, the amount may be from about 0.001 to 35 mg/kg of body weight administered one to six times per day. However, the dose administered to an animal, particularly a human, should be sufficient to effect a therapeutic response over a reasonable time frame. The dose will be determined by the strength of the particular compositions employed and the condition of the person, as well as the body weight of the person to be treated. The size of the dose also will be determined by the existence, nature and extent of any adverse side-effects that might accompany the administration of a particular composition. A suitable dosage of delta-9-tetrahydrocannabinol for administration by inhalation is 0.01 to 100 mg/kg per day, given in 2–4 divided doses. A preferred dosage is 0.01 to 35 mg/kg per day. A more preferred dosage is 0.05 to 5 mg/kg per day.

DESCRIPTION OF THE PREFERRED EMBODIMENTS

The following examples illustrate the present invention. They are not to be construed to limit the claims in any manner whatsoever. Semiaqueous solvent ratios are volumetric, i.e., v/v, and total 100 parts.

EXAMPLES 1–7

The physical stability of delta-9-tetrahydrocannabinol in varying ratios of ethanol, USP, purified water and propylene glycol is determined by placing 0.3 ml of delta-9-tetrahydrocannabinol (Standard, 100 mg/mL) in a 16×100 mm Pyrex tube, adding 2.7 mL of absolute ethanol for a total volume of 3.0 mL, and shaking the tube to mix. This results in a 100:0:0 ethanol (E); water (W): propylene glycol (PG) ratio and a drug concentration of 10 mg/mL. The foregoing steps are repeated for 12 more ratios according to the following Table 1, which lists volumes of standard delta-9-tetrahydrocannabinol (delta-9-THC), ethanol (Alcohol), purified water (Water), and propylene glycol, and the visual inspection results recorded after the samples are placed on a freeze/thaw (F/T) cycle for three turns.

TABLE 1

Delta-9-THC in Solvent Systems

| Example | Ratio (v/v) (Alcohol:Water: Polypropylene Glycol) | Visual Observation after 3 F/T cycles |
|---|---|---|
| 1A* | 100:0:0 | Clear |
| 1B* | 50:0:50 | Clear |
| 1 | 70:10:20 | Clear |

TABLE 1-continued

Delta-9-THC in Solvent Systems

| Example | Ratio (v/v) (Alcohol:Water: Polypropylene Glycol) | Visual Observation after 3 F/T cycles |
|---|---|---|
| 2 | 60:10:30 | Clear |
| 3 | 50:10:40 | Clear |
| 4 | 40:10:50 | Clear |
| 5 | 30:10:60 | Clear |
| 5* | 10:10:80 | Clear/oil droplets form when shaken |
| 6 | 60:20:20 | Clear |
| 7 | 40:20:40 | Clear |
| 7A* | 20:20:60 | Clear/oil droplets form when shaken |
| 7B* | 30:25:45 | Cloudy/oil droplets visible |
| 7C* | 35:30:35 | Cloudy |

*Comparison - 1A and 1B are not semiaqueous solvents and 5A, 7A, 7B and 7C are not stable after freeze/thaw.

As can be seen from Table 1, in varying ratios of ethanol/propylene glycol, delta-9-tetrahydrocannabinol is able to remain in solution in the presence of controlled amounts of water. However, as the water content increases and ethanol content decreases beyond a certain level, the drug readily falls out of solution.

EXAMPLES 8–14

The procedure of Examples 1–7 is repeated to assess solubility of increasing concentration of delta-9-tetrahydrocannabinol in a selected vehicle. Based on freeze/thaw data generated with delta-9-tetrahydrocannabinol using different solvent ratios (Table 1) a vehicle comprised of alcohol/water/propylene glycol in a volumetric ratio of 35:10:55 is selected. This ratio allows for good solubility of the drug while keeping the alcohol concentration low enough for ease of manufacturing. Results of the experiments are set forth in Table 2:

TABLE 2

Solubility of Delta-9-tetrahydrocannabinol in Alcohol:Water:Propylene Glycol (35:10:55) (v/v)

| Example | Delta-9-THC Conc. | Visual Observation |
|---|---|---|
| 8 | 0.16 mg/mL[1] | Clear, colorless soln. |
| 9 | 0.40 mg/mL[1] | Clear, colorless soln. |
| 10 | 0.80 mg/mL[1] | Clear, colorless soln. |
| 11 | 25 mg/mL[1] | Clear, light yellow soln. |
| 12 | 50 mg/mL | Clear, light yellow soln. |
| 13 | 75 mg/mL | Clear, light yellow soln. |
| 14 | 100 mg/mL | Clear, light yellow soln. |
| 14A* | 200 mg/mL | Cloudy, yellow soln. |

[1]Prepared by sequential dilution of Example 11
*Comparative Example (fails to enhance partionability)

The results show that if the alcohol concentration is reduced below approximately 35%, drug droplets begin to form indicating drug is below its solubility point in the vehicle. The results also indicate that delta-9-tetrahydrocannabinol concentrations in excess of 100 mg/mL are able to be manufactured with this formulation, but 200 mg/mL cannot.

From ease of manufacturing and expected doses of delta-9-tetrahydrocannabinol required for inhalation, a drug concentration of 25 mg/mL in the formulation of Example 8 (35:10:55 Alcohol:Water:Propylene Glycol) is evaluated in preclinical studies. A Pari LC Plus Nebulizer is used in a conventional fashion and generates aerosolized particles having a mean mass median aerodynamic diameter of 2.96 $\mu$M, which is well within the desired particle size for deep lung delivery.

Two animal species, rat and dog, are administered the formulation in a 14 day multiple dose inhalation study with a nebulizer. Results from the pharmacokinetic portion of the study indicate comparability between $t_{max}$ values found for intravenous and inhaled delivery. $T_{max}$ values are summarized for both single (intravenous and inhalation) and for multiple dose (intraveneous and inhalation) of delta-9-tetrahydrocannabinol in Table 3, as follows:

TABLE 3

Animal Studies of Exposure to Inhaled Delta-9-Tetrahydrocannabinol in Alcohol:Water:Propylene Glycol (35:10:55) (v/v)

| Species | Route of | Dose | Duration of Exposure | Average $t_{max}$ (minutes) | App. calc. $t_{max}$ (minutes)[1] |
|---|---|---|---|---|---|
| | | Single Dose Administration | | | |
| | Admin. | | | | |
| Dog | IV | 1 mg/kg | — | 1.8 | 1.8 |
| | Inhalation | 2 " | 8 minutes | 15.6 | 7.6 |
| Rat | IV | 2 mg/kg | — | 2.1 | 2.1 |
| | Inhalation | 0.5 " | 1.25 minutes | 5.7 | 4.45 |
| | Inhalation | 4.6 " | 15 minutes | 33.3 | 18.3 |
| | | Multiple Dose Inhalation | | | |
| | Admin.[2] | | | | |
| Dog | IV | 1 mg/kg | — | 1.8 | 1.9 |
| | Inhalation | 2 mg/kg | 8 minutes | 10.2 | 2.2 |
| | Inhalation | 5 " | 20 minutes | 22.2 | 2.2 |
| | Inhalation | 15 " | 60 minutes | 66 | 6 |
| Rat | IV | 2 mg/kg | — | 2.1 | 2.1 |
| | Inhalation | 2 mg/kg | 5 minutes | 6 | 1 |
| | Inhalation | 5 " | 15 minutes | 17.4 | 2.4 |
| | Inhalation | 15 " | 45 minutes | 46.2 | 1.2 |

[1]Apparent $t_{max}$ calculated as ($t_{max}$-duration of exposure). Blood samples drawn after entire dose is administered.
[2]IV data represents single dose administration.

The data in the foregoing examples show that a semi-aqueous formulation of delta-9-tetrahydrocannabinol in accordance with the present invention can produce a stable clear solution near the solubility point of the drug Moreover, because delta-9-tetrahydrocannabinol has poor affinity for the formulation, it is able to partition out and transport across cell membranes to reach the bloodstream quickly. This has been demonstrated by the comparative tow values achieved in single dose intravenous and 14 day multiple dose inhalation studies conducted in dogs and rats.

The above-mentioned patent and publications are incorporated herein by reference.

While there is described above the principles of this invention in connection with a specific drug and specific semiaqueous solvents, it is to be clearly understood that this description is made only by way of example, and not as a limitation to the scope of this invention. For example as a raw drug, synthetic or natural source-derived delta-9-tetrahydrocannabinol can be used, as well as prodrugs, isomers, derivatives, metabolites, and the like. Generally a wide variety of hydroxy containing solvents can be used, such as isopropanol instead of ethanol and polypropylene glycol instead of propylene glycol, so long as they are pharmaceutically-acceptable. All such variations are within the full intended scope of the appended claims.

What is claimed is:

1. A stable, aerosolizable composition, the composition consisting essentially of a therapeutically effective amount of delta-9-tetrahydrocannabinol in a pharmaceutically-acceptable semiaqueous solvent comprising volumetric ratios of about 10–70 parts of ethanol, about 10–30 parts of water and about 30–80 parts of propylene glycol having a combined total of 100, provided that:

(i) upon aerosolization the composition has a mean mass median aerodynamic diameter in the range from about 1 up to about 10 $\mu$M;

(ii) the ratio of the ethanol, water and propylene glycol produces a stable clear solution near the solubility point of the delta-9-tetrahydrocannabinol such that upon administration to the lung, the partitioning of the delta-9-tetrahydrocannabinol from the solvent is enhanced so as to reach the bloodstream; and (iii) the composition is pharmaceutically suitable for rapid bronchial delivery to the lung of a subject.

2. A composition as defined in claim 1 wherein the amount of delta-9-tetrahydrocannabinol comprises from about 0.1 to about 200 mg delta-9-tetrahydrocannabinol/mL of the solvent.

3. A composition as defined in claim 2 wherein the amount of delta-9- tetrahydrocannabinol comprises from about 0.1 to 25 mg delta-9-tetrahydrocannabinol/mL of the solvent.

4. A composition as defined in claim 2 wherein the amount of delta-9- tetrahydrocannabinol comprises about 50 mg delta-9-tetrahydrocannabinol/mL of the solvent.

5. A composition as defined in claim 1 wherein the volumetric ratios of ethanol:water:propylene glycol are selected from those in the range of from about 10–70: about 10: about 30–80, respectively, having a combined total of 100.

6. A composition as defined in claim 5 wherein the volumetric ratios of ethanol:water:propylene glycol are about 35: about 10: about 55, respectively, having a combined total of 100.

7. The composition of claim 1, wherein the mean mass median aerodynamic diameter is from about 1 $\mu$M to about 3 $\mu$M.

8. The composition of claim 1, wherein the ethanol is replaced with isopropanol.

9. The composition of claim 1, wherein the amount of delta-9-tetrahydrocannabinol is from about 0.05% to about 15%, by weight, of the composition.

10. The composition of claim 9, wherein the amount of delta-9-tetrahydrocannabinol is from about 0.02% to about 5%, by weight, of the composition.

11. The composition of claim 10, wherein the amount of delta-9-tetrahydrocannabinol is from about 0.1% to about 4%, by weight, of the composition.

12. The composition of claim 1, wherein the amount of delta-9-tetrahydrocannabinol is from about 0.01 mg to about 100 mg per kilogram of body weight of the subject.

13. The composition of claim 12, wherein the amount of delta-9-tetrahydrocannabinol is from about 0.025 mg to about 35 mg per kilogram of body weight of the subject.

14. The composition of claim 13, wherein the amount of delta-9-tetrahydrocannabinol is from about 0.05 mg to about 5 mg per kilogram of body weight of the subject.

15. The composition of claim 1, further consisting essentially of an agent selected from the group consisting of an buffer, pH adjusting agent, bacteriostatic agent, sodium chloride, and preservative.

16. The composition of claim 1, wherein the composition is administered to the subject one to five times a day.

17. The composition of claim 1, wherein the subject is a human.

18. A sterile and/or preserved sealed unit- or multi-unit dosage form of delta-9-tetrahydrocannabinol comprising a container and a stable composition for rapid delivery by inhalation to the lungs and subsequently to the bloodstream, as defined in claim 1.

19. A sterile and/or preserved sealed unit- or multi-unit dosage form as defined in claim 18 wherein said container comprises Type I Amber Glass.

20. A stable, aerosolizable composition, the composition consisting essentially of a therapeutically effective amount of delta-9-tetrahydrocannabinol in a pharmaceutically-acceptable semiaqueous solvent comprising volumetric ratios of about 10–70 parts of ethanol, about 10–30 parts of water and about 30–80 parts of a glycol selected from the group consisting of polypropylene glycol and polyethylene glycol having a combined total of 100, provided that:

(i) upon aerosolization the composition has a mean mass median aerodynamic diameter in the range from about 1 up to about 10 $\mu$M;

(ii) the ratio of the ethanol, water and propylene glycol produces a stable clear solution near the solubility point of the delta-9-tetrahydrocannabinol such that upon administration to the lung, the partitioning of the delta-9-tetrahydrocannabinol from the solvent is enhanced so as to reach the bloodstream; and (iii) the composition is pharmaceutically suitable for rapid bronchial delivery to a lung of a subject.

* * * * *